United States Patent
Peters et al.

(10) Patent No.: US 7,488,756 B2
(45) Date of Patent: Feb. 10, 2009

(54) USE OF NON-COMPETITIVE AND SELECTIVE GLUR5 ANTAGONISTS AS GLUTAMATE RECEPTOR MODULATING COMPOUNDS

(75) Inventors: Dan Peters, Malmö (SE); Elsebet Østergaard Nielsen, København K (DK); Alex Haahr Gouliaev, Veksø Sj. (DK)

(73) Assignee: Neurosearch A/S, Ballerup (DK)

( * ) Notice: Subject to any disclaimer, the term of this patent is extended or adjusted under 35 U.S.C. 154(b) by 372 days.

(21) Appl. No.: 10/466,864

(22) PCT Filed: Jan. 23, 2002

(86) PCT No.: PCT/DK02/00046

§ 371 (c)(1),
(2), (4) Date: Jul. 18, 2003

(87) PCT Pub. No.: WO02/058691

PCT Pub. Date: Aug. 1, 2002

(65) Prior Publication Data

US 2004/0048889 A1    Mar. 11, 2004

(30) Foreign Application Priority Data

Jan. 23, 2001  (DK) .............................. 2001 00117

(51) Int. Cl.
*A01N 37/12*   (2006.01)
*A01N 37/44*   (2006.01)
*A01N 37/18*   (2006.01)
*A61K 31/195*  (2006.01)
*A61K 31/16*   (2006.01)

(52) U.S. Cl. ...................................... 514/566; 514/616
(58) Field of Classification Search ................ 514/566, 514/616
See application file for complete search history.

(56) References Cited

U.S. PATENT DOCUMENTS 6,242,462 B1    6/2001  Bleakman et al.

FOREIGN PATENT DOCUMENTS

| GB | 2316616 A | 3/1998 |
| WO | WO 98/45270 A1 | 10/1998 |
| WO | WO 01/02367 A2 | 1/2001 |
| WO | WO 01/92273 A2 | 12/2001 |

OTHER PUBLICATIONS

Hardman, J. G., editor-in-chief, Goodman & Gilman's The Pharmacologoical Basis of Therapeutics, Ninth Edition, 1996, pp. 461, 467, 485.*
Stryer, L., Biochemistry, 4th Edition, 2000, pp. 196-197.*
Webster's II, New Riverside University Dictionary, 1988, pp. 933 and 944.*
Stanfa, L.C., et al. Neuroscience, vol. 93, No. 4, pp. 1391-1398, 1999.
Kubo Kazou, et al. retrieved from CAPLUS, accession No. 1978:169910, Database accession No. 88:169910 & Yamanouchi Seiyaku Kenyu Hokohu (1977), vol. date 1974, No. 3, pp. 8-12.
Hirschelman R, et al. retrieved from CAPLUS, accession No. 1972:21025, Database accession No. 76:21025 & Pharmazie, vol. 26, No. 8, 1971, pp. 491-492.
Ueda, et al. Journal of Polymer Science. vol. 17, 1163-1173 (1979).

* cited by examiner

*Primary Examiner*—Ardin Marschel
*Assistant Examiner*—Leslie A Royds
(74) *Attorney, Agent, or Firm*—Birch, Stewart, Kolasch & Birch, LLP

(57) ABSTRACT

This invention relates to the use of chemical compounds showing non-competitive and selective GluR5 antagonist or partial agonist activity for treating diseases that are responsive to modulation of an aspartate or a glutamate receptor. Moreover the invention provides chemical compounds for use according to the invention, as well as pharmaceutical compositions comprising the chemical compounds, and methods of treating diseases or disorders or conditions responsive to modulation of an aspartate or a glutamate receptor.

1 Claim, No Drawings

USE OF NON-COMPETITIVE AND SELECTIVE GLUR5 ANTAGONISTS AS GLUTAMATE RECEPTOR MODULATING COMPOUNDS

This application is the national phase under 35 U.S.C. §371 of PCT International Application No. PCT/DK02/00046 which has an International filing date of Jan. 23, 2002, which designated the United States of America.

TECHNICAL FIELD

This invention relates to the use of chemical compounds showing non-competitive and selective GluR5 antagonist or partial agonist activity for treating diseases that are responsive to modulation of an aspartate or a glutamate receptor. Moreover the invention provides chemical compounds for use according to the invention, as well as pharmaceutical compositions comprising the chemical compounds, and methods of treating diseases or disorders or conditions responsive to modulation of an aspartate or a glutamate receptor.

BACKGROUND ART

Excitatory neurotransmission in the mammalian central nervous system (CNS) is primarily mediated by the amino acid, L-glutamate, acting on ionotropic and metabotropic receptors. The ionotropic receptors, which respond to this amino acid, have been divided into the N-methyl-D-aspartate (NMDA) receptors, the alfa-amino-3-hydroxy-5-methyl-4-isoxazole propionic acid (AMPA) receptors, and the kainic acid (KA) receptors. Moreover molecular biological studies have established that these receptors are composed of subunits that can assemble to form functional channels, and a number of such subunits have been identified.

This way it has been established that the AMPA receptors are assembled from four protein subunits known as GluR1 to GluR4, while the KA receptors are assembled from subunits known as GluR5 to GluR7, KA-1 and KA-2.

Due to their distribution in different mammalian tissues, the GluR5 receptors and the substances acting thereon have drawn particular attention.

Thus GB 2316616 describes the use of a compound that modulates the glutamate GluR5 receptor in the hippocampus for the treatment of e.g. cognitive disorders, pain, neurological and psychiatric disorders and for drug screening.

WO 9845270 describes treatment of pain with specific GluR-5 receptor antagonists and new decahydroisoquinoline antagonists of this class.

WO 0102367 describes diester prodrugs of 3S,4aR,6S, 8aR-6-(((4-carboxy)phenyl)methyl)-1,2,3,4,4a,5,6,7,8,8a-decahydroisoquinoline-3-carboxylic acid, useful for treating pain, with improved bioavailability.

None of these references, however, describe non-competitive, selective GluR5 antagonists or partial agonists, or the use of such compounds.

SUMMARY OF THE INVENTION

The present invention describes non-competitive antagonists at the ionotropic glutamate subtype receptor GluR5 and their use.

According to the present invention it has now been found that the combination of a noncompetitive action and the level of antagonism/partial agonism allow for a modulation of existing biological activity, without necessarily completely blocking such activity. A major advantage of this modulating activity is the attenuation of endogenous activity, without completely abolishing such. For partial agonists, this allows e.g. acute pain transmission/perception without the induction of chronic pain via kainite receptor mediated "wind up phenomena", see e.g. the study described by Stanfa and Dickenson [Stanfa LC and Dickenson AH: The role of non-N-methyl-D-aspartate ionotropic glutamate receptors in the spinal transmission of nociception in normal animals and animals with carrageenan inflammation; *Neuroscience* 1999 93 (4) 1391-1398] on the involvement of GluR5 responses in the induction of "wind up phenomena".

Moreover, whereas the receptor occupancy of classical competitive antagonists will be lowered in burst situations (e.g. during induction of wind up phenomena), due to competition with the naturally occurring transmitter, non-competitive full antagonists have the advantage of maintaining the block of GluR5 transmission even in burst situations.

Another aspect of this invention is the selectivity for the GluR5 kainate subtype receptor. As explained above, AMPA-receptors are composed of GluR1-4 subunits and their splice variants, and it is well known that blockade of AMPA-responses inhibits the induction of long term potentiation and reduces cognitive functions in animals. Currently, most other compounds showing antagonism of GluR5 mediated responses, also blocks GluR1-4 mediated responses. A major advantage of the compounds for use according to this invention therefore is a lower incidence of side effects, e.g. reduction in cognitive functions.

Finally, the present invention is devoted to the provision of new compounds capable of antagonising the effect of excitatory amino acids, and to the use of such compounds for the treatment of diseases that are responsive to modulation of an aspartate or a glutamate receptor. In a preferred aspect the invention provides novel compounds useful as non-competitive, selective GluR5 antagonists.

Accordingly, in its first aspect the invention relates to the use of a chemical compound showing non-competitive and selective GluR5 antagonist or partial agonist activity, or a pharmaceutically-acceptable addition salt of such compound, for the manufacture of a medicament for the treatment, prevention or alleviation of a disease or a disorder or a condition of a mammal, including a human, which disease, disorder or condition is responsive to modulation of an aspartate or a glutamate receptor.

In another aspect the invention provides a pharmaceutical composition comprising a therapeutically-effective amount of a chemical compound of the invention or a pharmaceutically-acceptable addition salt thereof, together with at least one pharmaceutically-acceptable carrier or diluent.

In a further aspect the invention provides a method of diagnosis, treatment, prevention or alleviation of a disease or a disorder or a condition of a living animal body, including a human, which disorder, disease or condition is responsive to modulation of an aspartate or a glutamate receptor, comprising the step of administering to such a living animal body, including a human, in need thereof a therapeutically effective amount of a chemical compound of the invention, or a pharmaceutically-acceptable addition salt thereof.

Other objects of the invention will be apparent to the person skilled in the art from the following detailed description and examples.

Also, any possible combination of two or more of the embodiments described herein is comprised within the scope of the present invention.

DETAILED DISCLOSURE OF THE INVENTION

Non-Competitive Selective GluR5 Antagonists

In its first aspect, the invention relates to the use of a chemical compound showing non-competitive and selective GluR5 antagonist or partial agonist activity.

In the context of this invention a selective GluR5 antagonist or partial agonist activity is a compound showing significant effect in a functional GluR5 assay, preferably the functional GluR5 assay described in Example 1, and no significant effect in a functional GluR6 assay, preferably the functional GluR6 assay also described in Example 1.

In the context of this invention a compound showing significant effect in a functional GluR5 assay is a compound having an inhibitory concentration ($IC_{50}$) in the low micromolar and sub-micromolar range, preferably below 10 μM, more preferred below 5 μM, most preferred of below 1 μM.

In the context of this invention a compound showing no significant effect in a functional GluR6 assay is a compound having an inhibitory concentration ($IC_{50}$) above the low micromolar range, preferably above 10 μM, more preferred above 30 μM, most preferred of above 50 μM.

In the context of this invention a non-competitive GluR5 antagonist or partial agonist is a compound showing significant activity at the GluR5 receptor in a functional assay as described above, but which compound essentially does not bind the to GluR5 receptor, and thus does not compete with GluR5 receptor binding compounds. Such compounds may also be designated allosteric modulators of the GluR5 receptor.

The ability of a compound to bind to the GluR5 receptor may be determined by the ability of the compound to displace a GluR5 receptor binding compound, i.e. a GluR5 receptor agonist. One such GluR5 receptor agonist useful as reference compound is 2-amino-3-(3-hydroxy-5-tert-butylisoxazol-4-yl)propionic acid (ATPA).

In the context of this invention a compound showing essentially no binding at the GluR5 receptor is a compound which inhibits the specific binding of 3 nM $^3$H-ATPA by 50% in a concentration above the low micromolar range, preferably above 10 μM, more preferred above 30 μM, most preferred of above 50 μM, when determined in a binding assay as described in Example 2.

Compounds for Use According to the Invention

In another aspect, the invention provides chemical compounds for use according to the invention. In a preferred embodiment the chemical compound of the invention is represented by the general formula Ia, Ib, Ic or Id:

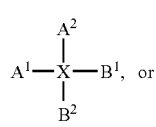
(Ia)

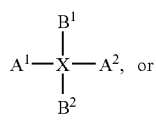
(Ib)

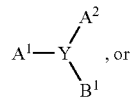
(Ic)

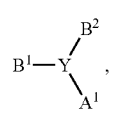
(Id)

in which formulas X can be any of the following groups:

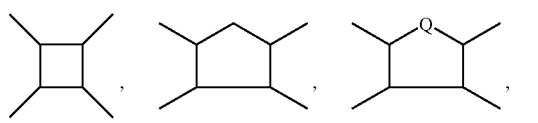

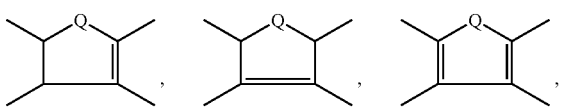

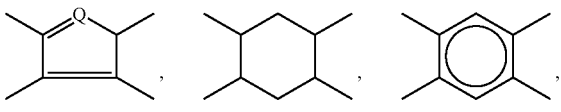

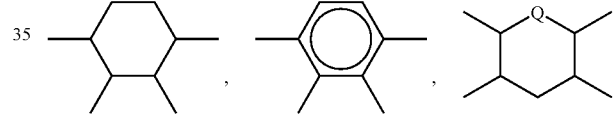

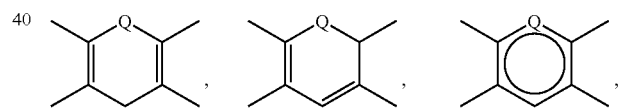

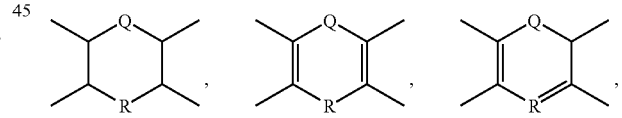

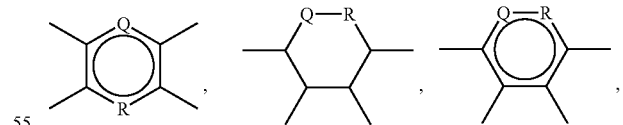

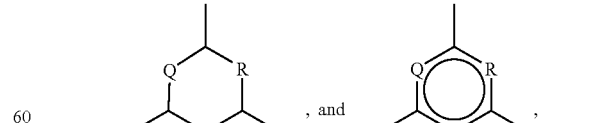

in which groups Q and R, independently of each another, represents O, S, $SO_2$, Se, N and/or NR', and wherein R' represents hydrogen, alkyl, cycloalkyl, or cycloalkyl-alkyl;

and in which formulas Y can be any of the following groups:

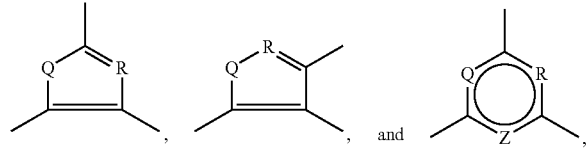

in which groups Q, R and Z, independently of each another, represents O, S, SO₂, Se, N, and/or NR', and wherein R' represents hydrogen, alkyl, cycloalkyl, or cycloalkyl-alkyl;

and in which formulas $A^1$ and $A^2$, independently of each another, represents —COOR¹, —SO₂NHR¹, —SO₃R¹, —B(OR¹)₂, —PO(OH)NHR¹, —PO(OH)OR¹, —CONHCN, or a group of the formula

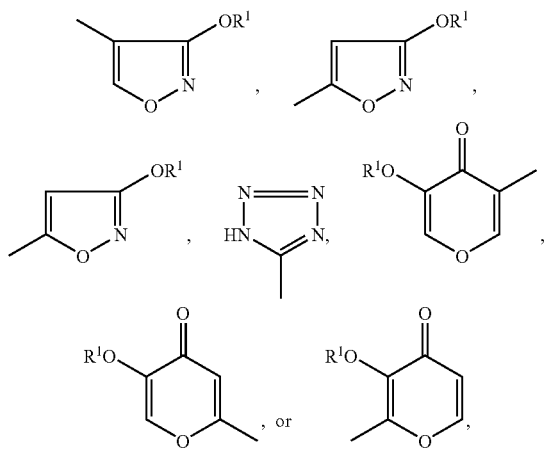

in which formulas $R^1$ represents hydrogen, alkyl, cycloalkyl, or cycloalkyl-alkyl;

and in which formulas $B^1$ and $B^2$, independently of each another, represents a group of the general formula -E-D, wherein D is a linker, read in either direction, that represents —C₁₋₆-alkyl-, —C₂₋₆-alkenyl-, —C₂₋₆-alkynyl-, —O—, —S—, —O—C₁₋₆-alkyl-, —C₁₋₆-alkyl-O—, —S—C₁₋₆-alkyl-, —C₁₋₆-alkyl-S—, —NR²—, —NR²—C₁₋₆-alkyl-, —C₁₋₆-alkyl-NR²—, —NR²CO—, —CONR²—, —NR²SO₂—, —SO₂NR²—, —C₁₋₆-alkyl-SO—, —SO—C₁₋₆-alkyl-, —C₁₋₆-alkyl-SO₂—, —SO₂—C₁₋₆alkyl-, —N=N—, or —NH—NH—, wherein $R^2$ represents hydrogen, alkyl, cycloalkyl, or cycloalkyl-alkyl; and E represents a mono- or polycyclic carbocyclic group, or a mono- or a polycyclic heterocyclic group;

or any pharmaceutically acceptable salt thereof.

In a more preferred embodiment, X represents

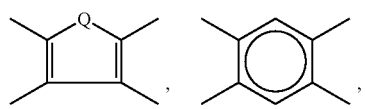

-continued

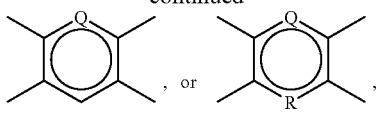

wherein Q and R, independently of each another represents O, S, NH, and/or N.

In another preferred embodiment $A^1$ and $A^2$, independently of each another, represents —COOH, or tetrazolyl.

In a third preferred embodiment $B^1$ and $B^2$, independently of each another, represents a group of the general formula -E-D, in which formula D is represents —NR²CO—, or —NR²SO₂—, wherein $R^2$ represents hydrogen, alkyl, cycloalkyl, or cycloalkyl-alkyl; and E represents a mono- or polycyclic aromatic carbocyclic group.

In a fourth preferred embodiment the chemical compound of the invention has a symmetric chemical structure, i.e. in which compound $A^1$ and $A^2$, and/or $B^1$ and $B^2$ represents identical substituents.

In a most preferred embodiment the chemical compound of the invention is 5-carboxyl-2,4-di-benzamido-benzoic acid (Compound A);

5-carboxyl-3,4-di-benzamido-2-furoic acid (Compound B);

4-carboxyl-2,5-di-benzamido-3-furoic acid (Compound C);

5-carboxyl-3,4-di-benzamido-2-thiophene carboxylic acid (Compound D);

4-carboxyl-2,5-di-benzamido-3-thiophene carboxylic acid (Compound E);

2,4-dibenzenesulfonamido-5-carboxyl-benzoic acid (Compound F);

1,3-dibenzamido-4,6-di-(5,5'-tetrazolyl)-benzene (Compound G);

2,6-dibenzamido-3,5-dicarboxyl-pyrazine (Compound H); or 2,6-dicarboxyl-3,5-dibenzamido-pyridine (Compound I);

or any pharmaceutically acceptable salt thereof.

Definition of Substituents

In the context of this invention an alkyl group designates a univalent saturated, straight or branched hydrocarbon chain. The hydrocarbon chain preferably contain of from one to eighteen carbon atoms (C₁₋₁₈-alkyl), more preferred of from one to six carbon atoms (C₁₋₆-alkyl; lower alkyl), including pentyl, isopentyl, neopentyl, tertiary pentyl, hexyl and isohexyl. In a preferred embodiment alkyl represents a C₁₋₄alkyl group, including butyl, isobutyl, secondary butyl, and tertiary butyl. In a preferred embodiment of this invention alkyl represents a C₁₋₃-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to six carbon atoms (C₂₋₆-alkenyl), including at least one double bond. In a most preferred embodiment the alkenyl group of the invention is ethenyl; 1,2- or 2,3-propenyl; or 1,2-,2,3-, or 3,4-butenyl.

In the context of this invention an alkynyl group designates a carbon chain containing one or more triple bonds, including di-ynes, tri-ynes and poly-ynes. In a preferred embodiment the alkynyl group of the invention comprises of from two to six carbon atoms ($C_{2-6}$-alkynyl), including at least one triple bond. In its most preferred embodiment the alkynyl group of the invention is ethynyl, 1,2- or 2,3-propynyl, 1,2-, 2,3- or 3,4-butynyl.

In the context of this invention a cycloalkyl group designates a cyclic alkyl group, preferably containing of from three to seven carbon atoms ($C_{3-7}$cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention a mono- or poly-carbocyclic group designates a mono- or polycyclic hydrocarbon group, which may in particular b an aromatic hydrocarbon group, i.e. a mono- or polycyclic aryl group, or a saturated hydrocarbon group, or a partially saturated hydrocarbon group. Preferred poly-carbocyclic group are the bicyclic poly-carbocyclic groups.

In the context of this invention a mono- or polycyclic aryl group designates a monocyclic or polycyclic aromatic hydrocarbon group. Examples of preferred aryl groups of the invention include phenyl, naphthyl and anthracenyl.

In the context of this invention a mono- or poly-heterocyclic group is a mono- or polycyclic compound, which holds one or more heteroatoms in its ring structure. Preferred heteroatoms include nitrogen (N), oxygen (O), and sulphur (S). One or more of the ring structures may in particular be aromatic (i.e. a heteroaryl), saturated or partially saturated. Preferred heterocyclic monocyclic groups of the invention include 5- and 6 membered heterocyclic monocyclic groups. Preferred poly-heterocyclic groups of the invention are the bicyclic heterocyclic groups.

Examples of preferred aromatic heterocyclic 5-membered monocyclic groups of the invention include furan, in particular 2-,3-,4- or 5-furanyl; thiophene, in particular 2-,3-,4-, or 5-thienyl; pyrrole, in particular 1-,2-,3-,4- or 5-pyrrolyl; oxaxole, in particular oxazol-(2-,4- or 5-)yl; thiazole, in particular thiazol-(2-,4-, or 5-)yl; imidazole, in particular imidazol-(1-,2-,4- or 5-)yl; pyrazole, in particular pyrazol-(1-, 3-,4- or 5-)yl; isoxazole, in particular isoxazol-(3-,4- or 5-)yl; isothiazole, in particular isothiazol-(3-,4- or 5-)yl; 1,2,3-oxadiazole, in particular 1,2,3-oxadiazol-(4- or 5-)yl; 1,2,3-triazole, in particular 1,2,3-triazol-(1-,4- or 5-)yl; and 1,3,4-thiadiazole, in particular 1,3,4-thiadiazol-(2- or 5-)yl.

Examples of preferred aromatic heterocyclic 6-membered monocyclic groups of the invention include pyridine, in particular pyridin-(2-,3-,4-,5- or 6-)yl; pyridazine, in particular pyridazin-(3-,4-,5- or 6-)yl; pyrimidine, in particular pyrimidin-(2-,4-,5- or 6-)yl; pyrazine, in particular pyrazin-(2-,3-,5- or 6-)yl; and 1,3,5-triazine, in particular 1,3,5-triazin-(2-,4- or 6-)yl.

Examples of preferred saturated or partially saturated heterocyclic monocyclic 5-membered groups of the invention include 2H-pyrrole, in particular 2H-pyrrol-(2-,3-,4- or 5-)yl; 2-pyrroline, in particular 2-pyrrolin-(1-,2-,3-,4- or 3-pyrroline, in particular 3-pyrrolin(1-,2-,3-,4- or 5-)yl; pyrrolidine, in particular pyrrolidin-(1-,2-,3-,4- or 5-)yl; 1,3-dioxolan, in particular 1,3-dioxolan-(2-,4- or 5-)yl; imidazolidine, in particular imidazolidin-(1-,2-,3-,4- or 5-)yl; 2-imidazoline, in particular 2-imidazolin-(1-,2-,4- or 5-)yl; 3-imidazoline, in particular 3-imidazolin-(1-,2-,4- or 5-)yl; 4-imidazoline, in particular 4-imidazolin-(1-,2-,4- or 5-)yl; pyrazolidine, in particular pyrazolidin-(1-,2-,3,4- or 5-)yl; 2-pyrazoline, in particular 2-pyrazolin-(1-, 3-, 4- or 5-)yl; and 3-pyrazoline, in particular 3-pyrazolin-(1-,3-,4- or 5-)yl.

Examples of preferred saturated or partially saturated heterocyclic monocyclic 6-membered groups of the invention include 2H-pyrane, in particular 2H-pyran-(2-,3-,4-,5- or 6-)yl; 4H-pyrane, in particular 4H-pyran-(2-,3-,4-,5- or 6-)yl; piperidine, in particular piperidin-(1-,2-,3-,4-,5- or 6-)yl; 1,4-dioxolane, in particular 1,4-dioxolan-(2-,3-,5- or 6-)yl; morpholine, in particular morpholin-(2-,3-,4-,5- or 6-)yl; 1,4-dithiane, in particular 1,4-dithian-(2-,3-,5- or 6-)yl; thiomorpholine, in particular thiomorpholin-(2-,3-,4-,5- or 6-)yl; piperazine, in particular piperazin-(1-,2-,3-,4-,5- or 6-)yl; 1,3,5-trithiane, in particular 1,3,5-trithian-(2-,4- or 6-)yl; and 1,4-oxazine, in particular 1,4-oxazin-(2-,3-,5- or 6-)yl.

Examples of preferred aromatic heterocyclic bi-cyclic groups of the invention include indolizine, in particular indolizin-(1-,2-,3-,5-,6-,7- or 8)yl; indole, in particular indol-(1-,2-,3-,4-,5-,6- or 7)yl; isoindole, in particular isoindol-(1-, 2-,3-,4-, 5-, 6- or 7-)yl; benzo[b]furan (benzofuran), in particular benzo[b]furan-(2-,3-,4-,5-,6- or 7-)yl; benzo[c]furan (isobenzofuran), in particular benzo[c]furan-(1-,3-,4-,5-,6- or 7-)yl; benzo[b]thiophene (benzothiophene), in particular benzo[b]thiophen-(2-,3-,4-,5-,6- or 7-)yl; benzo[c]thiophene (isobenzothiophene), in particular benzo[c]thiophen-(1-,3-, 4-,5-,6- or 7-)yl; benzimidazole, in particular benzimidazol-(1-,2-,4-,5-,6- or 7-)yl; benzthiazole, in particular benzthiazol-(2-,4-,5-,6- or 7-)yl; purine, in particular purin-(2-,6- or 8-)yl; quinoline, in particular quinolin-(2-,3-,4-,5-,6-,7- or 8-)yl; isoquinoline, in particular isoquinolin-(1-,3-,4-,5-,6-, 7- or 8-)yl; cinnoline, in particular cinnolin-(3-,4-,5-,6-,7- or 8-)yl; phthlazine, in particular phthlazin-(1-,4-,5-,6-,7- or 8-)yl; quinazoline in particular quinazolin-(2-,4-,5-,6-,7- or 8-)yl; quinoxaline, in particular quinoxalin-(2-,3-,5-,6-,7- or 8-)yl; 1,8-naphthyridine, in particular 1,8-naphthyridin-(2-, 3-,4-,5-,6- or 7-)yl; and pteridine, in particular pteridin-(2-, 4-,6- or 7-)yl.

Examples of preferred aromatic heterocyclic tri-cyclic groups of the invention include carbazole, in particular carbazol-(1-,2-,3-,4-,5-,6-,7-,8- or 9-)yl; acridine, in particular acridin-(1-,2-,3-,4-,5-,6-,7-,8- or 9-)yl; phenazine, in particular phenazin-(1-,2-,3-,4-,6-,7-,8- or 9-)yl; phenothiazine, in particular phenothiazin-(1-,2-, 3-,4-,6-,7-,8-,9- or 10-)yl; and phenoxazine, in particular phenoxazin-(1-,2-,3-,4-,6-,7-,8-, 9- or 10-)yl.

Examples of preferred saturated or partially saturated heterocyclic bi-cyclic groups of the invention include indoline, in particular indolin-(1-,2-,3-,4-,5-,6- or 7-)yl; 3H-indole, in particular 3H-indod-(2-,3-,4-,5-,6- or 7-)yl; 1H-indazole, in particular 1H-indazol-(3-,4-,5-,6- or 7-)yl; 4H-quinolizine, in particular 4H-quinolizin-(1-,2-,3-,4-6-,7-,8- or 9-)yl; quinuclidine, in particular quinuclidin-(2-,3-,4-,5-,6-,7- or 8-)yl; isoquinuclidine, in particular isoquinuclidin-(1-,2-,3-,4-,5-, 6-,7- or 8-)yl; tropane, in particular tropan-(1-,2-,3-,4-,5-,6-, 7- or 8-)yl; and nortropane, in particular nortropan-(1-,2-,3-, 4-,5-,6- or 7-)yl.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a chemical compound of the invention includes alkali metal salts, such as the sodium salt of a chemical compound of the invention containing a carboxy group.

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in *"Enantiomers, Racemates, and Resolutions"*, John Wiley and Sons, New York (1981).

Optical active compounds can also be prepared from optical active starting materials.

Methods of Preparation

Some of the chemical compounds of the invention are readily available while others may be prepared by conventional methods for chemical synthesis, e.g. those described in the working examples. The starting materials for the processes described in the present application are known or may readily be prepared by conventional methods from commercially available chemicals.

The end products of the reactions described herein may be isolated by conventional techniques, e.g. by extraction, crystallisation, distillation, chromatography, etc.

In a preferred embodiment the compounds for use according to the present invention may be obtained by the method disclosed by Ueda & Imai [Ueda M & Imai Y: Synthesis of polyamides by ring-opening polyaddition of bis-3,1-benzoxazin-4-ones with aliphatic diamines; *J. Polym. Sci.* 1979 17 (4) 1163-1173].

Biological Activity

The inventors found that the compounds of the present invention were capable of modulating the aspartate and/or glutamate receptors. In a preferred embodiment the invention the compounds were found useful as non-competitive GluR5 antagonists.

It is currently believed that compounds that modify neurotransmission by interaction with the aspartate and glutamate receptors are useful in the treatment of a variety of disorders of the CNS and PNS and disorders of other origin, including chronic or acute pain, neuropathic pain, intractable pain, migraine headaches, neurological and psychiatric disorders, depression, anxiety, psychosis, schizophrenia, excitatory amino acid-dependent psychosis, cognitive disorders, dementia, senile dementia, AIDS-induced dementia, stress-related psychiatric disorders, stroke, global and focal ischaemic or haemorrhagic stroke, cerebral hypoxia/ischaemia, cerebral infarction or cerebral ischaemia resulting from thromboembolic or haemorrhagic stroke, cardiac infarction, brain trauma, brain oedema, cranial/brain trauma, spinal cord trauma, bone-marrow lesions, hypoglycaemia, anoxia, neuronal damage following hypoglycaemia, hypotonia, hypoxia, perinatal hypoxia, cardiac arrest, acute and chronic neurodegenerative diseases or disorders and brain ischaemia of various origin, CNS degenerative disorders, Parkinson's disease, Alzheimer's disease, Huntington's disease, idiopathic and drug induced Parkinson's Disease, amyotrophic lateral sclerosis (ALS), post-acute phase cerebral lesions or chronic diseases of the nervous system, cerebral deficits subsequent to cardiac bypass surgery and grafting, perinatal asphyxia, anoxia from drowning, pulmonary surgery and cerebral trauma, hypoxia-induced nerve cell damage (e.g. in cardiac arrest or bypass operation, or neonatal distress), epilepsy, status epilepticus, seizure disorders, cerebral vasospasm, CNS-mediated spasms, motility disorders, muscular spasms, urinary incontinence, convulsions, disorders responsive to anticonvulsants, autoimmune diseases, emesis, nausea, obesity, chemical dependencies and addictions, addictions and withdrawal symptoms, drug or alcohol induced deficits, drug addiction, ocular damage, retinopathy, retinal neuropathy, tinnitus, tardive dyskinesia.

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers therefor, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route which suite the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition may be prepared by the skilled person using standard and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

In another aspect the invention provides a method for the diagnosis, treatment, prevention or alleviation of a disease or a disorder or a condition of a living animal body, including a human, which disorder, disease or condition is responsive to modulation of an aspartate or a glutamate receptor, comprising the step of administering to such a living animal body, including a human, in need thereof a therapeutically effective amount of a chemical compound of the invention, or a pharmaceutically-acceptable addition salt thereof.

In a more preferred embodiment, the disorder, disease or condition is chronic or acute pain, neuropathic pain, intractable pain, migraine headaches, neurological and psychiatric disorders, depression, anxiety, psychosis, schizophrenia, excitatory amino acid-dependent psychosis, cognitive disorders, dementia, senile dementia, AIDS-induced dementia, stress-related psychiatric disorders, stroke, global and focal ischaemic or haemorrhagic stroke, cerebral hypoxia/ischaemia, cerebral infarction or cerebral ischaemia resulting from thromboembolic or haemorrhagic stroke, cardiac infarction, brain trauma, brain oedema, cranial/brain trauma, spinal cord trauma, bone-marrow lesions, hypoglycaemia, anoxia, neuronal damage following hypoglycaemia, hypotonia, hypoxia, perinatal hypoxia, cardiac arrest, acute and chronic neurodegenerative diseases or disorders and brain ischaemia of various origin, CNS degenerative disorders, Parkinson's disease, Alzheimer's disease, Huntington's disease, idiopathic and drug induced Parkinson's Disease, amyotrophic lateral sclerosis (ALS), post-acute phase cerebral lesions or chronic diseases of the nervous system, cerebral deficits subsequent to cardiac bypass surgery and grafting, perinatal asphyxia, anoxia from drowning, pulmonary surgery and cerebral trauma, hypoxia-induced nerve cell damage (e.g. in cardiac arrest or bypass operation, or neonatal distress), epilepsy, status epilepticus, seizure disorders, cerebral vasospasm, CNS-mediated spasms, motility disorders, muscular spasms, urinary incontinence, convulsions, disorders responsive to anticonvulsants, autoimmune diseases, emesis, nausea, obesity, chemical dependencies and addictions, addictions and withdrawal symptoms, drug or alcohol induced deficits, drug addiction, ocular damage, retinopathy, retinal neuropathy, tinnitus, tardive dyskinesia.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

Example 1

Functional GluR5/GluR6 Assays

In this example the inhibition of domoate-induced increase in intracellular free calcium concentration ($Ca_i$) is used as a measure for glutamate antagonist activity of test substances. Domoate is a close analog of kainite, and a potent glutamate agonist.

Human embryonic HEK293 cells stably expressing GluR5 receptors and GluR6 receptors, respectively, in their un-edited forms, are used.

In this example the activity of Compound A of the invention (5-carboxyl-2,4-di-benzamido-benzoic acid), obtained according to Ueda & Imai [Ueda M & Imai Y: Synthesis of polyamides by ring-opening polyaddition of bis-3,1-benzoxazin-4-ones with aliphatic diamines; *J. Polym. Sci.* 1979 17 (4) 1163-1173], is compared to the action of ATPA, a GluR5 receptor agonist, and CNQX, a GluR5 receptor antagonist that inhibits the activity of the agonist.

Fluorometric methods for measuring $Ca_i$ have been developed [see e.g. Tsien et al., *J. Cell. Biol.* 1982 94 325]. The calcium-chelating fluorochromes (tetracarboxylic acids) are loaded into the cells as acetoxymethyl esters and subsequently released by unspecific intracellular esterase's. The free acids, which are impermeable to the cell membrane, are maintained in the cell for hours. The fluorescence spectrum (either $EX_{max}$, $EM_{max}$ or both) is changed by the binding of calcium. The fluorescence is then directly proportional to the $Ca_i$.

The present method uses the fluorochromes Fluo-3 or Fluo-4 as the calcium-chelator. Fluo-3/Fluo-4 is virtually nonfluorescent without calcium but the calcium-Fluo-3/Fluo-4 complexes show a bright fluorescence ($EM_{max}$=526 nm) after excitation around 500 nm ($EX_{max}$=505 nm). This fluorescence spectrum is similar to the spectrum of fluorescein. Since excitation and emission is in the visible light region of the spectrum standard equipment without quarts optics may be used.

Cell Culture

The HEK293 cells stably expressing GluR5 or GluR6 expressing are grown in Dulbecco's Modified Eagle Medium (DMEM) containing 10% foetal calf serum, in polystyrene culture flasks (175 $cm^2$) in a humidified atmosphere of 5% $CO_2$ in air, at 37° C. Confluency of cells should be 80-90% on day of plating. GluR5 or GluR6 cells are rinsed with 10 ml of phosphate buffered saline (PBS), then added 1.5 ml of Trypsin-EDTA and left in the incubator for 5 min. After addition of 10 ml of growth media, cells are resuspended by trituration with a 10 ml pipette 15 times.

The cells are seeded at a density of 0.5-1×$10^6$ cells/ml (100 µl/well) in black-walled, clear bottom, 96-well plates pre-treated with 0.001% PEI solution (75 µl/well for ≧30 min). Plated cells were allowed to proliferate for 24 h before loading with dye.

Loading with Fluo-4-AM

Fluo-4-AM (1 mg; Molecular Probes) is added 912 μl DMSO containing 25 mg/150 μl Pluoronic F-127 (Molecular Probes). The Fluo-4-AM stock solution (1 mM) is diluted with DMEM to a final concentration of 2 μM Fluo-4-AM.

The media is removed from the wells, and 50 μl of the Fluo-4-AM loading solution is added to each well. The plate is sealed and incubated at room temperature for 60 minutes.

Calcium Measurements

After the loading period, the loading media is aspirated and the cells are washed twice with 100 μl Na$^+$ free Ringer solution (NN: 10 mM HEPES, 140 mM Choline chloride, 5 mM KCl, 1 mM MgCl$_2$, 10 mM CaCl$_2$, pH 7.4) to remove extracellular dye. 100 μl NN is added to each well, and the fluorescence is measured in the FLIPR (Fluorescence Image Plate Reader).

Cells are pre-incubated for 1.5 minutes with test compound (50 μl) before addition of domoate (50 μl) to a final concentration of 2 μM.

Stock solutions of test substances are made in 48% ethanol, 50% DMSO or 100% DMSO. The final concentration of ethanol or DMSO in the well must not exceed 0.1%. Dilutions are done in NN in clear V-bottom plates.

FLIPR (Fluorescence Image Plate Reader: Molecular Devices) Settings

Temperature: 25° C.

Preincubation: 50 μl test solution at a rate of 30 μl/sec and starting height of 100 μl Antagonist phase: 50 μl domoate solution (8 μM) at a rate of 35 μl/sec and starting height of 150 μl Reading intervals: preincubation—10 sec.×7 and 3 sec.×3 antagonist phase—3 sec.×17 and 10 sec.×12

Addition plates (diluted compound plate and domoate plate) are placed on the far right and left positions in the FLIPR tray. Cell plates are placed in the middle position. The preincubation phase test is run first using the above settings. The FLIPR picks up the desired amount from the compound plate and pipettes into the cell plate. The FLIPR then make the appropriate determinations in accordance with the above settings.

Calculation

Fluorescence arising from stimulation with domoate or test substance is corrected for the mean basal fluorescence (in NN). Fluorescence of domoate in the presence of test substance is expressed relative to the domoate response alone.

The test value is given as the IC$_{50}$ value (the concentration (μM) of the test substance which inhibits 50% of the domoate induced Ca$_i$ elevation) calculated either from a concentration/response curve or from the formula $$IC_{50} = (\text{applied test substance concentration, μM}) \times \frac{1}{\left(\frac{C_o}{C_x} - 1\right)}$$

where $C_o$ is domoate stimulated Ca$_i$ accumulation in control assays, and $C_x$ is the domoate stimulated Ca$_i$ in the presence of test compound (the calculation assumes normal mass-action interaction). 25-75% inhibition of the domoate stimulation must be obtained before calculation of an IC$_{50}$.

The results of this determination are presented in Table 1 below.

Example 2

GluR5 Binding Assay

The weak AMPA receptor agonist 2-amino-3-(3-hydroxy-5-tert-butylisoxazol-4-yl)propionic acid (ATPA) is known to be a very potent GluR5 receptor agonist, binding to the receptor with a Kd of 4.3 nM [Clarke et al., *Nature* 1997 389 599-603]. In this example $^3$H-ATPA is used to label the agonist binding site at homomeric GluR5 receptors expressed in heterologous systems [Hoo et al.; *Neuropharmacolopy* 1999 38 1811-1817].

Cell Cultures and Membrane Preparation

The HEK293 cells stably expressing GluR5 or GluR6 expressing were cultured (37° C.; 5% CO$_2$) in Dulbecco's Modified Eagle Medium (DMEM) with Glutamax I™, 4500 mg/l D-glucose, 25 mM HEPES; without sodium pyruvate (Life Technologies Cat No 32430-027), with 10% foetal bovine serum.

When the cultures reach confluency in large culture flasks (175 cm$^2$), DMEM is removed and the cells are washed once in Dulbecco's PBS (KCl 0.2 g/l; KH$_2$PO$_4$ 0.2 g/l; NaCl 8 g/l; Na$_2$HPO$_4$ 1.15 g/l). Cells are harvested by addition of 3 ml Hank's Balanced Salt Solution (HBSS) with Trypsin (0.5 g/l) and EDTA (0.2 g/l; Life Technologies Cat No 25300-054) to the culture for approximately 5 minutes. 15 ml of Dulbecco's PBS is added and the cell suspension is transferred to Falcon tubes and centrifuged at 3000 rpm for 10 minutes. The pellet is washed once in 15 ml Tris-HCl buffer (50 mM, pH 7.4) using an Ultra-Turrax homogenizer and centrifuged at 2° C. for 10 minutes at 27,000×g. The washed pellet is resuspended in 15 ml Tris-HCl buffer (50 mM, pH 7.4) and kept at −80° C. until it is used for the binding experiment.

Assay

On the day of the experiment the cell membranes are thawed and centrifuged at 2° C. for 10 minutes at 27,000×g. The pellet is washed once by homogenization in Tris-HCl buffer (50 mM, pH 7.4) and centrifugation for 10 minutes (27,000×g; 2° C.). The final pellet is resuspended using an Ultra-Turrax homogenizer in Tris-HCl buffer (50 mM; pH 7.4) to 30-100 μg protein per assay and used for binding assays. Aliquots of 0.5 ml cell suspension are added to 25 μl of test solution and 25 μl of $^3$H-ATPA (3 nM, final concentration), mixed and incubated in duplicate for 60 minutes at 2° C.

Non-specific binding is determined using L-glutamate (0.6 mM, final concentration). After incubation the samples are added 5 ml of ice-cold Tris-HCl buffer (50 mM, pH 7.4) and poured directly onto Whatman GF/C glass fibre filters under suction and immediately washed with 5 ml ice-cold buffer.

The amount of radioactivity on the filters is determined by conventional liquid scintillation counting. Specific binding is total binding minus non-specific binding.

Results 25-75% inhibition of specific binding must be obtained before calculating the IC$_{50}$.

The test value will be given as IC$_{50}$ (the concentration (μM) of test substance, which inhibits the specific binding of 3 nM $^3$H-ATPA by 50%.

$$IC_{50} = (\text{applied test substance concentration, μM}) \times \frac{1}{\left(\frac{C_o}{C_x} - 1\right)}$$

where $C_o$ is specific binding in control assays and $C_x$ is the specific binding in the test assay.

The result of this determination is presented in Table 1 below.

TABLE 1

Functional and Binding Data

| Compound | GluR5 Activity | GluR6 Activity IC$_{50}$ (μM) | GluR5 Binding |
|---|---|---|---|
| ATPA | 0.7 | >30 | 0.024 |
| CNQX | 3.3 | 7.6 | 0.72 |
| Compound A | 1.9 | >30 | >10 |

These results show that Compound A is a non-competitive antagonist of the GluR5 receptor, because it shows activity at the receptor, but no binding to the receptor, and it is selective because it shows activity only at the GluR5 receptor, not at the GluR6 receptor.

The invention claimed is:

1. A pharmaceutical composition comprising a therapeutically-effective amount of 5-carboxyl-2,4-di-benzamido-benzoic acid, or a pharmaceutically-acceptable addition salt thereof, together with at least one pharmnaceutically-acceptable carrier or diluent.

* * * * *